United States Patent [19]

Mormann et al.

[11] Patent Number: 5,723,067
[45] Date of Patent: Mar. 3, 1998

[54] TRIS-(CYANOTO)-S-TRIAZINES AND ANISOTROPIC DUROPLASTIC NETWORKS OBTAINED WITH THEM

[75] Inventors: Werner Mormann, Kreuztal; Joerg Zimmermann, Siegen, both of Germany

[73] Assignee: Europaeische Wirtschaftsgemeinschaft, Luxemburg, Luxembourg

[21] Appl. No.: 612,913
[22] PCT Filed: Sep. 7, 1994
[86] PCT No.: PCT/EP94/02980
   § 371 Date: May 1, 1996
   § 102(e) Date: May 1, 1996
[87] PCT Pub. No.: WO95/07268
   PCT Pub. Date: Mar. 16, 1995

[30] Foreign Application Priority Data

Sep. 8, 1993 [LU] Luxembourg .................. 88 404

[51] Int. Cl.⁶ .................. C08G 73/08; C07D 251/04
[52] U.S. Cl. .................. 252/299.01; 544/219; 528/423; 528/422; 528/149
[58] Field of Search .................. 544/219; 528/423, 528/422, 149; 252/299.01

[56] References Cited

U.S. PATENT DOCUMENTS 5,136,011  8/1992  Barclay et al. .................. 528/162

FOREIGN PATENT DOCUMENTS 0409069  1/1991  European Pat. Off. .

OTHER PUBLICATIONS

G.G. Barclay et al. (1992) Macromol. 25, 2947–2954.
D. Janietz et al. (1993) Liquid Crystals 13, 499–505.

Primary Examiner—Mark Nagumo
Attorney, Agent, or Firm—McAulay Fisher Nissen Goldberg & Kiel, LLP

[57] ABSTRACT

Tris-(cyanato)-s-triazines having the formula:

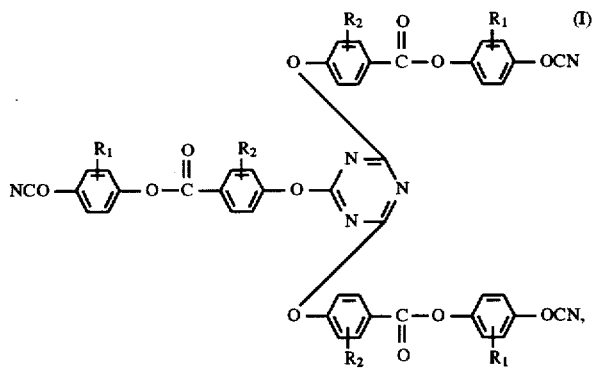

wherein $R_1$ and $R_2$ independently of one another, represent halogen, in particular, chlorine, bromine and fluorine, hydrogen or a methyl group or ethyl group. The monomers disclosed always provide an anisotropic network. Methods for the polycyclotrimerization of polycyanates to obtain the inventive compounds are also disclosed.

22 Claims, 1 Drawing Sheet

TRIS-(CYANOTO)-S-TRIAZINES AND ANISOTROPIC DUROPLASTIC NETWORKS OBTAINED WITH THEM

FIELD OF THE INVENTION

The invention is directed to a process for the production of anisotropic duroplastic networks by polycyclotrimerization of polycyanates in the melt and to the products obtained by this process. Where appropriate, the polycyclotrimerization of the invention takes place in the presence of catalysts, comonomers and other conventional additives.

BACKGROUND OF THE INVENTION

The relevant prior art is given, e.g., by EP-A-0 409 069 (Hefner, et al.), in which Mesogenic bifunctional cyanic acid esters are described. The majority of the process products described therein are isotropic, with only one example concerning the production of an anisotropic network (op. cit., page 66, lines 41ff)). According to that example, monomers of a dicyanate of 4,4'-dihydroxybenzanilide are used, which melt at a comparatively high temperature of 184° C.

OBJECTS OF THE INVENTION

The object of the present invention is to provide monomers and additional comonomers by which an anisotropic network can always be obtained. Another object of the invention is to lower the melting point of the starting monomers, or mixture of monomers and comonomers, so that conversion to the desired products occurs at the lowest possible temperatures. Yet another object is to use nonmesogenic starting materials.

BRIEF DESCRIPTION OF THE DRAWING

The figure shows a comparison of the variation in storage modulus as a function of temperature for the inventive composition and a prior art composition.

DETAILED DESCRIPTION OF THE INVENTION

Figure 1:
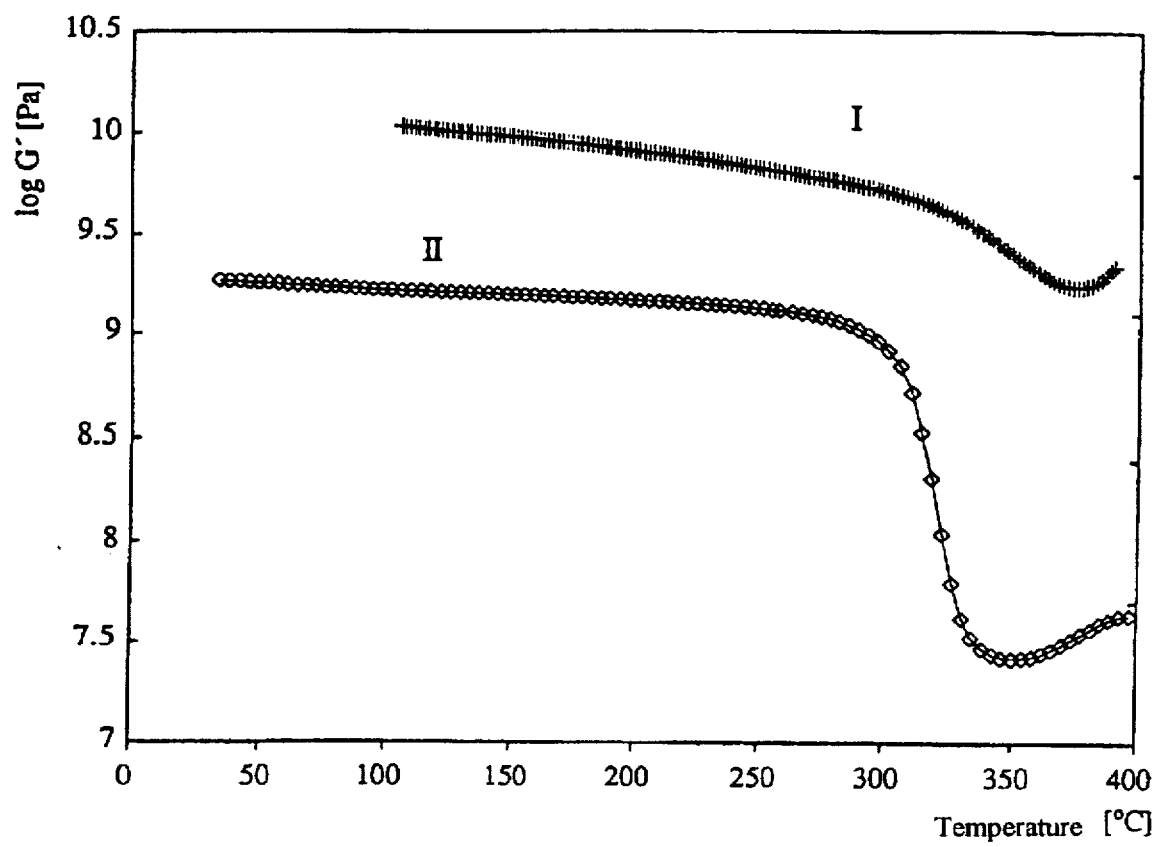

According to the invention, this object is met by tris (cyanato)-s-triazines having the following formula (I):

The object of the invention is further met by a process in which polycyanates in the form of liquid-crystalline tris (cyanato)-s-triazines having the above formula (I) are polycyclotrimerized.

In carrying out the process according to the invention, the polycyclotrimerization is effected in the melt. With respect to the compounds in the above formula (I), the polycyclotrimerization is preferably carried out between approximately 90° and 300° C., most preferably between approximately 120° and 220° C. The temperature advisably does not fall below approximately 90° C., as it would then be impossible to rule out the presence of crystalline components which are poorly accessible to a further reaction. This would result in a deterioration of the mechanical properties of the process product. If the maximum temperature of approximately 300° C. is exceeded, the clarification point of the mixture would be exceeded. Therefore, it is advantageous to keep to the range of approximately 90° to 300° C. and especially to the range of approximately 120° to 220° C.

The process according to the invention can easily be carried out exclusively thermally and does not absolutely require the use of catalysts. The use of catalysts accelerates the polycyclotrimerization in a desirable manner and is therefore preferred. Suitable catalysts include, for example, acids, bases, salts, nitrogen compounds and phosphorous compounds. Specific examples include Lewis acids such as $AlCl_3$, $BF_3$, $FeCl_3$, $TiCl_4$, $ZnCl_2$, and $SnCl_2$. Brönsted acids such as HCl and $H_3PO_4$; aromatic hydroxy compounds such as phenol, p-nitrophenol, catechol, and dihydroxynaphthalene; sodium hydroxide; sodium methanolate; sodium phenolate; trimethylamine; triethylamine; tributylamine; diazabicyclo[2.2.2]octane; chinoline; isochinoline; tetrahydroisochinoline; tetraethylammonium chloride; pyridine-N-oxide; tributylphosphine; and metal octanoates; naphthenates, and acetylacetonates, particularly in the form of the corresponding salts of zinc, tin, copper and cobalt. Other suitable catalysts include metal chelates such as the chelates of transition metals and two-pronged and three-pronged ligands, preferably chelates of iron, cobalt, zinc, copper, manganese, zirconium, titanium, vanadium, aluminum, and magnesium. These and other catalysts are described in U.S. Pat. Nos. 3,694,410 and 4,094,852. The metal naphthenates, metal octoates and/or metal acetylacetonates are preferred, most preferably in the form of the

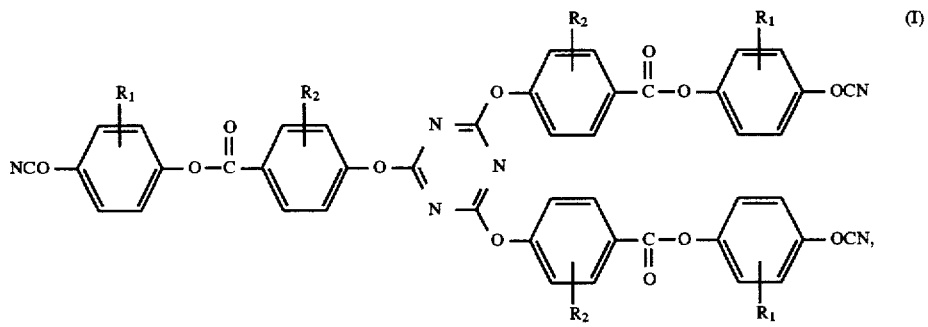

(I)

where $R_1$ and $R_2$, independently of one another, represent a halogen, in particular chlorine, bromine and fluorine, hydrogen or a methyl or ethyl group.

It is surprising for one skilled in the art that this product has liquid-crystalline properties, since similar products have been described in the literature as nonliquid-crystalline (Barclay, G. G., Ober, C. K., Papathomas, K. I., Wang, D. W., *Macromolecules* 1992, 25, 2974–2954).

corresponding copper compounds. There are preferably approximately 0.01 to 3 parts by weight of catalysts, most preferably, approximately 0.05 to 1 part by weight of catalyst, for 100 parts by weight of the reactive components of the monomeric starting mixture.

In addition to the tris-(cyanato)-s-triazines of formula (I), the reactive components of the starting mixture optionally include which will be comonomers which will be It has been shown surprisingly that tris-(cyanato)-s-triazines according to the invention can be polycyclotrimerized with nonliquid-crystalline dicyanato comonomers while nevertheless forming an anisotropic duroplastic network. Dicyanato comonomers having the following formula (II) are preferred:

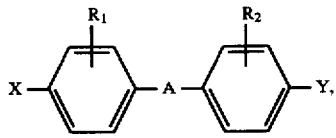 (II)

where X and Y, independently of one another, represent OCN or

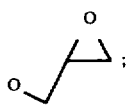

Y represents an alkyl, alkyloxy, alkyloxycarbonyl or acyloxy group with a chain length of 1 to 20 carbon atoms, possibly branched;

A represents the following structural elements:

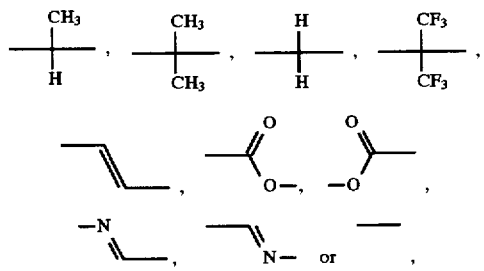

$R_1$ and $R_2$, independently of one another, represent hydrogen, a halogen, preferably chlorine, bromine or fluorine, or a methyl or ethyl group. 4,4'-Dicyanatophenylbenzoate, 4,4'-dicyanatobiphenyl, and 2,2bis(4-cyanatophenyl)propane are most preferred.

The tris-(cyanato)-s-triazines according to the invention can contain a relatively high proportion of nonliquid-crystalline cyanato comonomers. There are preferably approximately 30 to 300 parts by weight, most preferably approximately 50 to 100 parts by weight, of nonliquid-crystalline dicyanato comonomers to 100 parts by weight tris-(cyanato)-s-triazines according to the invention.

The advantage in the admixture of nonliquid-crystalline dicyanato comonomers (II) in the polycyclotrimerization is that anisotropic networks are obtained using considerable quantities of inexpensive monomers which by themselves only produce isotropic networks. A further advantage in the use of additional comonomers (II) is the ability to adapt the characteristics of the process product and thus the crosslinkage density and the softening temperature in a directed manner. In order to achieve these advantages, the quantitative proportion of tris-(cyanato)-s-triazine of formula (I) and the dicyanato comonomer (II) is selected so as to ensure the anisotropic character of the desired duroplastic process product.

In another advantageous development of the invention, other liquid-crystalline cyanato comonomers are converted with the tris-(cyanato)-s-triazines or with a combination of the tris-(cyanato)-s-triazines and nonliquid-crystalline dicyanato comonomers (II) according to the invention. The liquid-crystalline cyanato comonomers taken into consideration are those having the following formula (III) in particular:

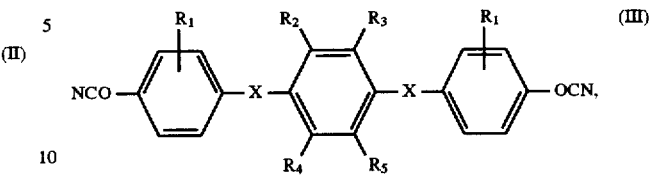 (III)

where X represents the following structural elements:

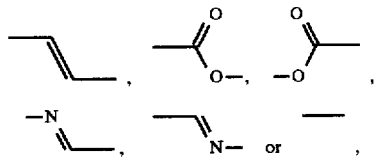

$R_1$ to $R_5$, independently of one another, represent hydrogen, a halogen, preferably chlorine, fluorine or bromine, or a methyl group, ethyl group, propyl group or butyl group or $R_2$, $R_3$, $R_4$ or $R_5$ represent a benzene group, $R_2$ to $R_5$ represent hydrogen when $R_1$ is not hydrogen, $R_1$ represents hydrogen when $R_2$ to $R_5$ do not represent hydrogen.

Preferred comonomers (III) are 1,4-bis(cyanatobenzoyloxy)benzene and 1,4'-bis(cyanatobenzoyloxy)methylbenzene. The use, according to the invention, of compounds of formula (I) advantageously lowers the melting point of the liquid-crystalline comonomers (III) which otherwise can only be processed at temperatures above their melting point which is generally above 200° C. There are preferably up to approximately 1000 parts by weight, most preferably approximately 100 to 500 parts by weight, of the comonomers of formula (III) to 100 parts by weight of the tris-(cyanato)-s-triazines according to the invention.

Within the framework of the invention, the polycyclotrimerization preferably lasts for a period of approximately 0.5 to 2 hours when a catalyst is used.

In order to improve the characteristics of the duroplastic product aimed for, it may be advantageous in individual cases to carry out after-baking at an increased temperature as is known in the prior art for isotropic networks. For example, curing is effected for 2 hours at 150° C., for 2 hours at 200° C., and for another two hours at 240° C.

For the purpose of improving the characteristics, an electromagnetic field can also be applied during the polycyclotrimerization (see, e.g., Finkelmann, et al., Macromol. Chem. 180, 803–806 (1979): methacrylate copolymers containing lc side chains are oriented in the electrical field; Moore, et at., ACS Polymeric Material Science and Engineering, 52, 84–86 (1985): orientation of side chain lc polymers in the magnetic field; S. K. Garg, S. Kenig, High Modulus Polymers, 71–103 (1988); Marcel Dekker, inc., Allgemeine Diskussion der Orientierung von 1 c-Polymeren durch Scherkräfte [General Discussion of the Orientation of lc Polymers by Shear Forces]). In this way, the thermal expansion and tensile strength, in particular, are improved and controlled in the direction of orientation.

Thus, an advantageous anisotropic duroplastic network in the form of a homopolymerizate or copolymerizate can be produced by way of the process according to the invention and with the tris-(cyanato)-s-triazines according to the invention.

The subject matter of the invention is also directed to anisotropic duroplastic networks in the form of a homopolymerizate or copolymerizate of tris-(cyanato)-s-triazines having the above formula (I), particularly in the form of a copolymerizate or the tris-(cyanate)-s-triazines of formula (I) and the nonliquid-crystalline dicyanato comonomers (II) and/or liquid-crystalline cyanato comonomers (III) as defined above. A preferred copolymerizate of this type is characterized in that it contains approximately 30 to 300 parts by weight, most preferably approximately 50 to 100 parts by weight, of the dicyanato comonomer (II) and/or up to approximately 1000 parts by weight, most preferably approximately 100 to 500 parts by weight, of the liquid-crystalline cyanato comonomers (III) to 100 parts by weight of the tris-(cyanato)-s-triazine of formula (I).

The following advantages can be achieved by means of the present invention: The invention makes it possible to reliably produce anisotropic networks. In so doing, it is not limited to liquid-crystalline starting materials; rather, nonliquid-crystalline or mesogenic starting materials can be used in addition. In this way, the product characteristics can be controlled in a directed manner, e.g., the crosslinkage density, with the result that hardness, brittleness, resistance to temperature, and glass temperature can be adjusted as desired. A related advantage consists in that the aforementioned comonomers with a relatively high melting point can be converted at substantially lower temperatures with the tris-(cyanato)-s-triazines, according to the invention, due to the reduced melting points of the reaction mixture. Further, it has been shown that the modulus of elasticity (measurement of strength) of the anisotropic duroplastic networks according to the invention is improved by a factor of 10 compared with the process products of the prior art.

The anisotropic duroplastic networks according to the invention can be used, according to conventional processing methods, as construction materials for the production of insulating materials, laminates, composites, coverings, and coatings.

The following examples are provided to illustrate the present invention and should not be construed to limit the scope of the invention of the present application in any way.

EXAMPLE 1

Production of the precursor in the form of 1,3,5-tris(4-hydroxyphenyloxy-4-carbonylphenoxy)-2,4,6-triazine: 6.1 g (12.5 moles) of 1,3,5-tris(4-carboxyphenoxy)-2,4,6-triazine is introduced in a dry 250-ml single-neck flask with a protective gas connection and magnetic stir rod. To this is added 4.9 g (41.1 moles) of thionyl chloride and a small spatula tip of 4-N,N-dimethylaminopyridine. The mixture is heated for 5 hours at 120° C. The surplus thionyl chloride is extracted by vacuum. 11.0 g (43.2 mmoles) of 1,4-bis(trimethylsiloxy)benzene is then added. A distilling apparatus is set up and maintained for 12 hours at 150° C. After distilling off the estimated quantity of chlorotrimethylsilane, the surplus 1,4-bis(trimethylsiloxy)benzene is extracted by oil pump vacuum. The raw product is identified by IR spectroscopy. For the purpose of desilylation, the raw product is dissolved in 200 ml of N,N-dimethylformamide and 30 ml of diluted hydrochloric acid and stirred at room temperature for several hours. The following processes are then carried out: precipitation in 400 ml of water, separation by filtration, washing twice in 100 ml of water in each instance, and drying under vacuum at 80° C. Identification is effected by IR spectroscopy.

Synthesis of 1,3,5-tris(4-cyanatophenyloxy-4-carbonylphenoxy)-2,4,6-triazine: 2.54 g (3.32 mmoles) of 1,3,5-tris(4-hydroxyphenyloxy-4-carbonylphenoxy)-2,4,6-triazine, 1.37 g (12.94 mmoles) of bromocyanogen are placed in 40 ml of N,N-dimethylformamide in a 250-ml single-neck flask with magnetic stir rod and ice water cooling at an internal temperature of 0°–5° C. To this is added 1.01 g (9.96 mmoles) of triethylamine by drops within a period of 5 minutes followed by stirring for 15 minutes. The 1,3,5-tris(4-cyanatophenyloxy-4-carbonylphenoxy)-2,4,6-triazine precipitates in 400 ml of ice water as a white precipitate. This is washed twice, each time with 50 ml of water, dried at room temperature by oil pump vacuum, and identified by IR spectroscopy. The glassy-amorphous compound softens at approximately 90° C. while forming nematic textures.

EXAMPLE 2

Formation and characterization of an anisotropic network of 1,3,5-tris(4-cyanatophenyloxy-4-carbonylphenoxy)-2,4,6-triazine: The amorphous product obtained in Example 1 is heated in a heating plate from 30° C. to 300° C. at a rate of 20° C. and is examined by polarizing light microscopy. The substance, which is solid at room temperature becomes liquid at 90° C., the melt exhibits textures typical of a nematic liquid-crystalline phase. At 200° C., the viscosity of the mixture increases and cyclotrimerization takes place. The mixture becomes solid at approximately 250° C. The textures appearing above the softening point persist throughout the entire curing period and also after cooling at room temperature. Repeated heating of the specimen to 300° C. has no effect on the frozen-in textures of the network.

Comparison Example 1

Production of a Test Rod of 1,3,5-tris(4-cyanatophenyloxy-4-carbonylphenoxy)-2,4,6-triazine: A sample of 1,3,5-tris(4-cyanatophenyloxy-4-carbonylphenoxy)-2,4,6-triazine is after-baked for 10 hours at 150° C. and then for 2 hours at 310° C. The resulting non-transparent test rod (23×13×2 mm) is tested under torsion (30° C. to 400° C., 2° C./min, 1 Hz). The storage modulus G' is 15.8 GPa at 100° C. The glass temperature is observed at 370° C.

Production of a test rod from 2,2-bis(4-cyanatophenyl)propane: A sample of 2,2-bis(4-cyanatophenyl)propane is after-baked for 10 hours at 150° C., and then for 2 hours at 310° C. The resulting non-transparent test rod (23×13×2 mm) is tested under torsion (30° C. to 400° C., 2° C./min, 1 Hz). The storage modulus G' is 1.6 GPa at 100° C., the glass temperature is observed at 320° C.

FIG. 1 shows a graph of the storage module as a function of temperature for the test rod of networks of 1,3,5-tris(4-cyanatophenyloxy-4-carbonylphenoxy)-2,4,6-triazine (I) and 2,2-bis(4-cyanatophenyl)propane (II) (DMTA experiment: heating rate 2 K/min, frequency 1 Hz). The storage module obtained with the product according to the invention is appreciably higher than that of the comparison product.

EXAMPLE 3

Formation and characterization of a network of 1,3,5-tris(4-cyanatophenyloxy4-carbonylphenoxy)-2,4,6-triazine with 4,4'-dicyanatobiphenyl: 20 g of 1,3,5-tris(4-cyanatophenyloxy-4-carbonylphenoxy)-2,4,6-triazine and 20 g of 4,4'-dicyanatobiphenyl are homogenized and cured for one hour at 180° C. and for one hour at 250° C. The nematic liquid-crystalline textures persist throughout the entire curing period. No change is brought about in the anisotropic characteristics by cooling of the sample or repeated heating to 300° C.

EXAMPLE 4

Formation and characterization of a network of 1,3,5-tris (4-cyanatophenyloxy-4-carbonylphenoxy-2,4,6-triazine with 4,4'-dicyanatophenylbenzoate: 10 g of 1,3,5-tris(4-cyanatophenyloxy-4-carbonylphenoxy)-2,4,6-triazine, 20 g of 4,4'-dicyanatophenylbenzoate, and 0.15 percent by weight of copper (II) acetylacetonate are homogenized and cured for 15 minutes at 150° C. and for one hour at 250° C. The nematic liquid-crystalline textures persist throughout the entire curing period. No change is brought about in the anisotropic characteristics by cooling of the sample or by repeated heating to 300° C.

EXAMPLE 5

Formation and characterization of a network of 1,3,5-tris (4-cyanatophenyloxy-4-carbonylphenoxy)-2,4,6-triazine with 2,2-bis(4-cyanatophenyl)propane: 20 g of 1,3,5-tris(4-cyanatophenyloxy-4-carbonylphenoxy)-2,4,6-triazine and 0.7 g of 2,2-bis(4cyanatophenyl)propane are homogenized and cured for one hour at 180° C. and for one hour at 250° C. The nematic liquid-crystalline textures persist throughout the entire curing period. No change is brought about in the anisotropic characteristics by cooling of the sample or by repeated heating to 300° C.

EXAMPLE 6

Formation and characterization of a network of 1,3,5tris (4-cyanatophenyloxy-4-carbonylphenoxy)-2,4,6-triazine with 2,2-bis(4-epoxypropoxy)propane: 20 g of 1,3,5-tris(4-cyanatophenyloxy-4-carbonylphenoxy)-2,4,6triazine and 0.4 g of 2,2-bis(4epoxypropoxy)propane are homogenized and cured for three hours at 130° C., for one hour at 180° C. and for one hour at 250° C. The nematic liquid-crystalline textures persist throughout the entire curing period. No change is brought about in the anisotropic characteristics by cooling of the sample or by repeated heating to 300° C.

We claim:

1. Tris(cyanato)-s-triazines of formula (I)

where $R_1$ and $R_2$, independently of one another, represent halogen, hydrogen or a methyl group or ethyl group.

2. Process for the production of anisotropic duroplastic networks, comprising polycyclotrimerization of polycyanates in the form of liquid-crystalline tris(cyanato)-s-triazines of formula (I) of claim 1.

3. Process according to claim 2, wherein the polycyclotrimerization is carried out between 90° and 300° C.

4. Process according to claim 3, wherein the polycyclotrimerization is carried out in the presence of a catalyst.

5. Process according to claim 4, further comprising the use of a catalyst selected from the group consisting of metal naphthenates, metal octoates, metal acetylacetonates and combinations thereof.

6. Process according to claim 5, wherein there are 0.01 to 3 parts by weight of catalysts for 100 parts by weight of the reactive components of the starting mixture.

7. The process according to claim 4, wherein there are 0.01 to 3 parts by weight of catalysts for 100 parts by weight of the reactive components of the starting mixture.

8. The process according to claim 4, wherein the polycyanates further comprise a liquid crystalline cyanato comonomer selected from the group consisting of 1,4-bis (cyanatobenzoyloxy)benzene, 1,4'-bis(cyanatobenzoyloxy) methylbenzene and combinations thereof.

9. Process according to claim 3 wherein the polycyclotrimerization is carried out for a period of approximately 0.5 to 2 hours.

10. Process according to claim 3 further comprising after-baking.

11. Process according to any one of claims 2 to 6, wherein the polycyanates further comprise nonliquid-crystalline comonomers, having the formula:

$$X-\text{Ar}-A-\text{Ar}-Y, \quad (II)$$

where X and Y, independently of one another, represent OCN or

Y represents an alkyl, alkyloxy, alkyloxycarbonyl or acyloxy group with chain lengths of 1 to 20 carbon atoms, A represents the following structural elements:

$R_1$ and $R_2$, independently of one another, represent hydrogen, halogen, or a methyl or ethyl group.

12. Process according to claim 11, wherein the comonomer (II) is selected from the group consisting of 4,4'-Dicyanatophenylbenzoate, 4,4'-dicyanatobiphenyl, 2,2 bis (4-cyanatophenyl)propane and combinations thereof.

13. The process according to claim 12, wherein there are 30 to 300 parts by weight of the dicyanato comonomer to 100 parts by weight of tris(cyanato)-s-triazine.

14. The process according to claim 12, wherein the polycyanates further comprise a liquid crystalline cyanato comonomer selected from the group consisting of 1,4-bis (cyanatobenzoyloxy)benzene, 1,4'-bis(cyanatobenzoyloxy) methylbenzene and combinations thereof.

15. Process according to claim 11, wherein there are 30 to 300 parts by weight of the comonomer (II) to 100 parts by weight of tris-(cyanato)-s-triazine of formula (I).

16. Process according to claim 11 wherein the polycyanates further comprise a liquid crystalline cyanato comonomer selected from the group consisting of 1,4-bis(cyanatobenzoyloxy) benzene, 1,4'-bis(cyanatobenzoyloxy) methylbenzene and combinations thereof.

17. Process according to claim 2 wherein an electromagnetic field is applied to the melt of tris(cyanato)-s-triazine of formula (I) during polycyclotrimerization.

18. The process according to claim 2, wherein the polycyanates further comprise a liquid crystalline cyanato comonomer selected from the group consisting of 1,4-bis(cyanatobenzoyloxy)benzene, 1,4'-bis(cyanatobenzoyloxy) methylbenzene and combinations thereof.

19. Anisotropic duroplastic network in the form of a homopolymerizate or copolymerizate of tris(cyanato)-s-triazine of formula (I)

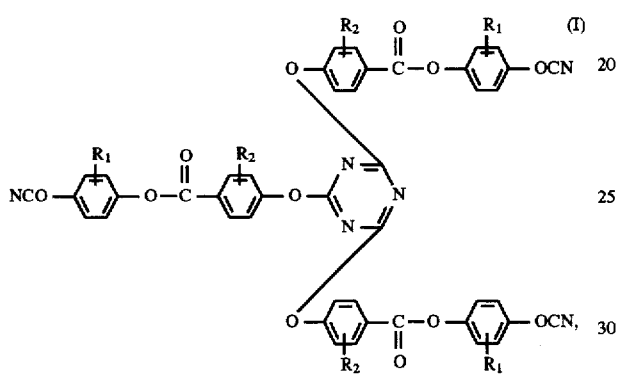

where $R_1$ and $R_2$, independently of one another, represent halogen, hydrogen or a methyl group or ethyl group.

20. An anisotropic duroplastic network comprising a copolymerizate of tris(cyanato)-s-triazines having the formula (I)

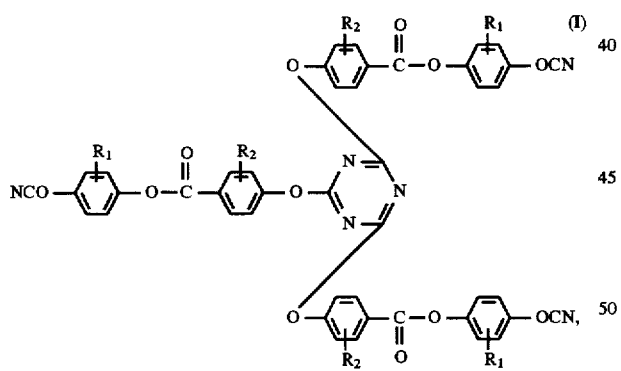

wherein $R_1$ and $R_2$ independently of one another, represent halogen, hydrogen or a methyl group or ethyl group;

and nonliquid-crystalline comonomers having the formula (II):

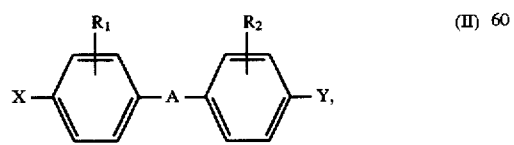

wherein X and Y, independently of one another, represent —OCN or

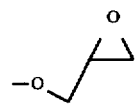

Y represents an alkyl, alkyloxy, alkyloxycarbonyl or acyloxy group with chain lengths of 1 to 20 carbon atoms.

A represents the following structural elements:

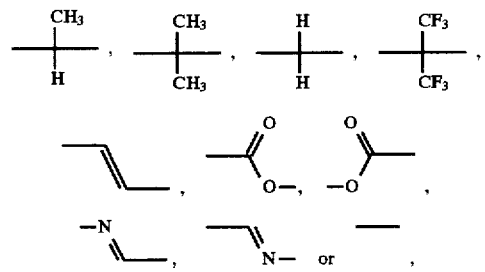

$R_1$ and $R_2$, independently of one another, represent hydrogen, halogen, or a methyl or ethyl group.

21. The anisotropic duroplastic network according to claim 20, having copolymerized therein 30 to 300 parts by weight of the comonomers having the formula (II):

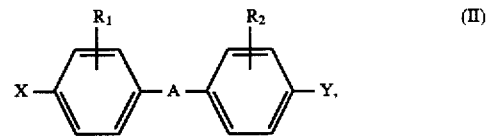

wherein X and Y, independently of one another, represent —OCN or

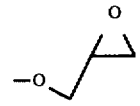

Y represents an alkyl, alkyloxy, alkyloxycarbonyl or acyloxy group with chain lengths of 1 to 20 carbon atoms.

A the following structural elements:

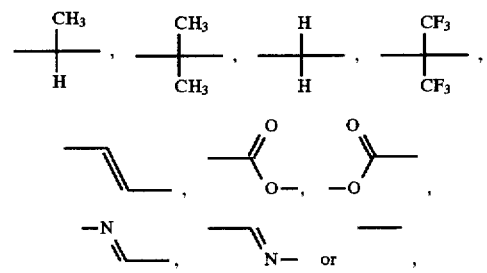

$R_1$ and $R_2$, independently of one another, represent hydrogen, halogen, or a methyl or ethyl group; and 0 to 1000 parts by weight of the liquid crystalline cyanato comonomers having formula (III):

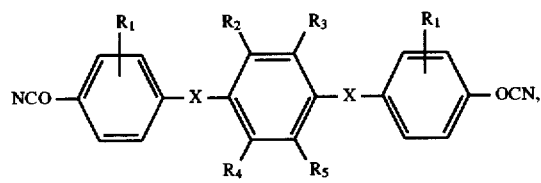

where X the following structural elements:

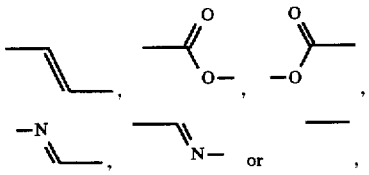

$R_1$ to $R_5$, independently of one another, represent hydrogen, halogen, especially chlorine, fluorine or bromine, or a methyl group, ethyl group, propyl group or butyl group or $R_2$, $R_3$, $R_4$ or $R_5$ represent a benzene group, $R_2$ to $R_5$ hydrogen when $R_5$ is not hydrogen, $R_1$ represents hydrogen when $R_2$ to $R_5$ do not represent hydrogen, to 100 parts weight of tris-(cyanato)-s-triazine of formula (I).

22. The anisotropic duroplastic network of claim 20, further comprising copolymerized therein liquid-crystalline cyanato comonomers having the formula (III):

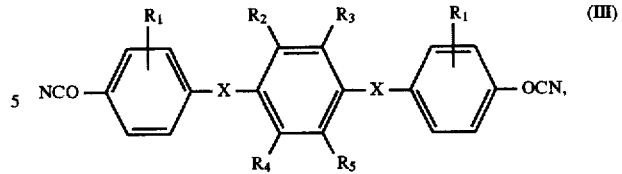

where X represents the following structural elements:

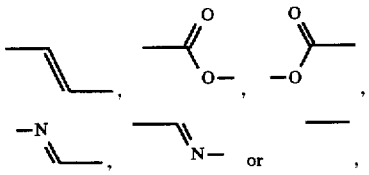

$R_1$ to $R_5$, independently of one another, represent hydrogen, halogen, especially chlorine, fluorine or bromine, or a methyl group, ethyl group, propyl group or butyl group or $R_2$, $R_3$, $R_4$ or $R_5$ represent a benzene group, $R_2$ to $R_5$ represent hydrogen when $R_1$ is not hydrogen, $R_1$ represents hydrogen when $R_2$ to $R_5$ do not represent hydrogen.

* * * * *